United States Patent [19]

Bezwada et al.

[11] Patent Number: 4,994,074
[45] Date of Patent: Feb. 19, 1991

[54] COPOLYMERS OF EPSILON-CAPROLACTONE, GLYCOLIDE AND GLYCOLIC ACID FOR SUTURE COATINGS

[75] Inventors: Rao S. Bezwada, Whitehouse Station; Alastair W. Hunter, Bridgewater; Shalaby W. Shalaby, Lebanon, all of N.J.

[73] Assignee: Ethicon, Inc., Somerville, N.J.

[21] Appl. No.: 473,291

[22] Filed: Feb. 1, 1990

[51] Int. Cl.$^5$ ............... C08G 63/06; C08G 63/08
[52] U.S. Cl. ........................ 606/230; 528/354
[58] Field of Search .............. 528/354; 606/230, 228, 606/231

[56] References Cited

U.S. PATENT DOCUMENTS

| 4,045,418 | 8/1977 | Sinclair | 528/354 X |
| 4,057,537 | 11/1977 | Sinclair | 528/354 |
| 4,243,775 | 1/1981 | Rosensaft et al. | 528/354 X |
| 4,300,565 | 11/1981 | Rosensaft et al. | 529/354 X |
| 4,595,713 | 6/1986 | St. John | 528/354 X |
| 4,605,730 | 8/1986 | Shalaby et al. | . |
| 4,624,256 | 11/1986 | Messier et al. | . |
| 4,700,704 | 10/1987 | Jamiolkowski et al. | . |
| 4,788,979 | 12/1988 | Jarret et al. | . |
| 4,791,929 | 12/1980 | Jarret et al. | . |

Primary Examiner—Earl Nielsen
Attorney, Agent, or Firm—Matthew S. Goodwin

[57] ABSTRACT

Copolymer of a predominant amount of ε-caprolactone, the balance being glycolide and glycolic acid. Coating for an absorbable, multifilament surgical suture prepared by dissolving the copolymer in an organic solvent.

16 Claims, No Drawings

COPOLYMERS OF EPSILON-CAPROLACTONE, GLYCOLIDE AND GLYCOLIC ACID FOR SUTURE COATINGS

BACKGROUND OF THE INVENTION

This invention relates to copolymers of ε-caprolactone and glycolide, and more specifically, to such copolymers with improved properties especially adapted for use as coatings for absorbable multifilament surgical sutures.

Multifilament surgical sutures such as Vicryl® poly(lactide-co-glycolide) multifilament suture typically require a surface coating to improve the pliability and knotting characteristics of the suture. A polymer coating which has recently been developed and shows significant promise as a suture coating is derived from a polymer solution of ε-caprolactone in an appropriate organic solvent. The coating solution is typically applied to the surface of the suture using conventional techniques, and then the solvent is removed. Polycaprolactone is a biocompatable polymer with a relatively low melting point, a property which is essential for good coating characteristics. Additionally, sutures coated with polycaprolactone exhibit enhanced pliability and handling characteristics. Unfortunately, polycaprolactone homopolymer is essentially nonabsorbable because it retains some of its mass and mechanical integrity in vivo for periods up to one year, which is too long for numerous surgical applications.

In an effort to improve the bioabsorbability and other properties of a polycaprolactone coating polymer, the polymer composition has been modified by incorporating copolymerizable monomers or lubricating agents therein. For example, U.S. Pat. No. 4,624,256 discloses a suture coating copolymer of at least 90 percent ε-caprolactone and a biodegradable monomer, and optionally a lubricating agent. Examples of monomers for biodegradable polymers disclosed include glycolic acid and glycolide, as well as other well known monomers typically used to prepare polymer fibers or coatings for multifilament sutures. U.S. Pat. No 4,791,929 discloses a bioabsorbable coating of a copolymer of at least 50 percent ε-caprolactone and glycolide. Sutures coated with such copolymers are reported to be less stiff than sutures coated with other materials, and the physical properties of the coated suture are also reported to be acceptable.

Unfortunately, the problem of adequate bioabsorbability of homopolymers and copolymers of ε-caprolactone for suture coating applications still remains. One of the difficulties a skilled polymer chemist has faced in solving this problem is in developing a faster absorbing polymer of ε-caprolactone without sacrificing the physical properties of multifilament sutures coated with such a polymer. In view of the deficiencies with the known art polycaprolactone coatings, it would be most desirable to accomplish this goal.

SUMMARY OF THE INVENTION

In one aspect, the invention is a copolymer of a predominant amount of ε-caprolactone, and the balance glycolide and glycolic acid. The copolymer is characterized by a concentration of glycolic acid such that the intrinsic viscosity of the copolymer in hexafluoroisopropyl alcohol (HFIP) is between about 0.15 to about 0.60 deciliters per gram (dl/g).

In another aspect, the invention is a coating for a surgical suture. This coating comprises a solution of the copolymer described above in an organic solvent.

Surprisingly, the use of glycolic acid as a comonomer into the copolymers of this invention increases the rate of absorption of the copolymers relative to the absorption rate of prior art copolymers of ε-caprolactone and glycolide. This increase in the rate of absorption is achieved while maintaining the physical properties of sutures coated with such copolymers, for example, tissue drag, which measures the degree of trauma associated with passing the coated suture through tissue, knot tiedown characteristics and tensile properties.

The copolymers of this invention and the coatings derived therefrom can be used for coating bioabsorbable, multifilament surgical sutures.

DETAILED DESCRIPTION OF THE INVENTION

A predominant amount of ε-caprolactone generally refers to an amount of ε-caprolactone greater than 50 mole percent of the comonomer composition from which the copolymer of this invention is derived. ε-Caprolactone is the predominant component of the copolymer because of its low melting temperature and its ability to enhance the physical properties of coated multifilament sutures. Preferably, the amount of ε-caprolactone used ranges from about 80 to about 95, more preferably from about 90 to about 95 mole percent.

The remaining comonomers of the copolymer of this invention are glycolide and glycolic acid. The amount of glycolic acid in the comonomer composition from which the copolymer is derived is an amount such that the intrinsic viscosity of the copolymer in a 0.1 g/dl solution of HFIP at 25° C. is between about 0.15 to about 0.60 dl/g. Preferably, the intrinsic viscosity of the copolymer is between about 0.20 to about 0.50 dl/g. The glycolic acid can be used in part to control the molecular weight of the copolymer, and therefore its intrinsic viscosity, and, in combination with the glycolide comonomer, can be used to lower the melting temperature of the copolymer relative to that of a polycaprolactone homopolymer. Advantageously, the crystalline melting temperature of the copolymer is between about 30° to about 60° C., preferably between about 35° to about 50° C. The frequency of the hydrolytically labile linkages associated with the use of glycolic acid along the chains of the copolymer is also responsible for enhancing the absorption profile of the coating.

The adjustment of the intrinsic viscosity of the copolymer by varying the concentration of glycolic acid is important to achieve a copolymer coating that will not only form a film on the outer surface of the suture but also penetrate and distribute evenly into the interstices of the multifilament fibers. This penetration and the subsequent adsorption of the coating polymer onto individual fibers of the multifilament increases the pliability of the suture and enhances its knotting characteristics, specifically the ease with which a knot can slide down the length of the suture during an operative procedure. Likewise, the control of the crystalline melting temperature, which to a significant degree is controlled by the intrinsic viscosity, by varying the relative proportions of glycolide and glycolic acid is important to achieve similar improvements in the properties of coated sutures.

Advantageously, the amount of glycolic acid in the comonomer composition from which the copolymer is derived to achieve an acceptable intrinsic viscosity and to increase the rate of absorption relative to the prior art copolymers of ε-caprolactone and glycolide ranges from about 1 to about 15, preferably from about 2 to about 10 mole percent. The glycolide comonomer not only lowers the melting temperature of the copolymer, but also, to a lesser extent relative to glycolic acid, increases the rate of absorption and is preferably present in the comonomer composition at a concentration ranging from about 5 to about 20, more preferably from about 5 to about 10 mole percent. The mole ratio of glycolide to glycolic acid to achieve desired coating properties advantageously ranges from about 20:80 to about 95:5, preferably from about 70:30 to about 90:10.

The copolymers of this invention can be prepared by polymerizing in the presence of an organometallic catalyst the desired amounts of ε-caprolactone, glycolide and glycolic acid at an elevated temperature, e.g. 160° to 190° C., for a time sufficient to achieve the desired intrinsic viscosity. The organometallic catalyst is preferably a tin-based catalyst, preferably stannous octoate, and is present in the reaction mixture at a mole ratio of monomer to catalyst between 10,000 to 90,000 to 1, preferably 15,000 to 30,000 to 1.

The organic solvent for the polymer coating of this invention is advantageously a solvent which has a normal boiling point no greater than 120° C. Examples of suitable organic solvents include but are not limited to chlorinated aliphatic solvents such as 1,1,2-trichloroethane, aromatic solvents such as toluene, and aliphatic ketones such as acetone.

The coating can easily be prepared by simply dissolving the copolymer of this invention into the appropriate organic solvent. The concentration of the copolymer in solution desirably ranges from about 1 to about 20, preferably from about 10 to about 15 weight percent. Generally, concentrations greater than 20 weight percent polymer provide coating solutions which are too viscous to achieve adequate penetration of the coating solution into the interstices of the fibers, and concentrations below 1 weight percent are inadequate to properly coat a sufficient amount of copolymer onto the suture, although it may be possible but inconvenient to employ two or more coating steps to achieve a sufficient coating concentration on the copolymer. Once a solution of the copolymer is prepared, a suture can be coated using conventional coating techniques, e.g. dipping, spraying, etc. After the coating is applied, the solvent can be removed by drying in air, or by other techniques well known in the art, for example, removing the solvent at an elevated temperature under vacuum.

The suture to be coated can be a monofilament or multifilament suture. Preferably, a multifilament suture in a braided, twisted, crocheted, knitted or covered form is used. Preferably, the suture is an absorbable, multifilament braided suture. The preferred absorbable sutures are those prepared from a polymer of a lactone or a polymer of one or more lactones Examples of the most widely used lactones for suture preparation are lactide, glycolide and ε-caprolactone. The most preferred suture is Vicryl® poly(lactide-co-glycolide) multifilament braided suture. For numerous surgical applications, the suture is attached to one or more needles.

The following examples illustrate the claimed invention and are in no way intended to limit its scope.

EXAMPLE 1

COPLYOMER OF ε-CAPROLACTONE/GLYCOLIDE/GLYCOLIC ACID AT 0.90/0.05/0.10 MOLE RATIO

A flame dried, 250 ml, round bottom single neck flask is charged with 102.73 g (0.9 mole) of ε-caprolactone, 5.80 g (0.05 mole) of glycolide, 7.61 g (0.10 mole) of glycolic acid, and 0.121 milliliters of stannous octoate (0.33 molar in toluene). The flask is fitted with a flame dried mechanical stirrer. The reactor is purged with nitrogen three times before venting with nitrogen. The reaction mixture is heated to 160° C. and maintained at this temperature for 24 hours. The copolymer is isolated, characterized, and tested for absorption. The results are reported in Table 1.

EXAMPLE 2

COPOLYMER OF ε-CAPROLACTONE/GLYCOLIDE/GLYCOLIC ACID AT 0.90/0.08/0.04 BY MOLE

The procedure of Example 1 is repeated, except that the reaction flask is charged with 9.29 g (0.08 mole) of glycolide and 3.04 g (0.04 mole) of glycolic acid.

COMPARATIVE EXAMPLE 1

COPOLYMER OF ε-CAPROLACTONE/GLYCOLIDE AT 90/10 BY WT. (90/10 BY MOLE)

A flame dried, 250 ml, round bottom, single neck flask is charged with 90 g (0.789 mole) of ε-caprolactone, 10 g (0.0862 mole) of glycolide, 7.96 ml (40 millimole/mole of total monomer) of distilled 1-dodecanol, and 0.121 ml of stannous octoate (0.33 molar solution in toluene). The reaction flask is purged with nitrogen three times before venting with nitrogen. The reaction mixture is heated to 180° C. and maintained there for 4.5 hours. The copolymer is isolated, characterized, and tested for absorption. The results are reported in Table 1.

TABLE 1

| CHARACTERIZATION AND ABSORPTION OF COATING COPOLYMERS | | | |
|---|---|---|---|
| Example No. | 1 | 2 | Comparative Example 1 |
| Characterization | | | |
| Copolymer comp. caprolactone/glycolide/GA[1] | 90/5/10 by mole | 90/8/4 by mole | 90/10/0 by wt. (90/10/0 by mole) |
| Intrinsic Viscosity of copolymer in HFIP. dl/g | 0.19 | 0.31 | 0.28 |
| Melting Point[2] | 41–44° C. | 42–40° C. | 35–45° C. |
| Absorption | | | |
| In Vitro hydrolysis at 100° C. (sterile water) Percent nonhydrolyzed | | | |

TABLE 1-continued

| CHARACTERIZATION AND ABSORPTION OF COATING COPOLYMERS | | | |
|---|---|---|---|
| Example No. | 1 | 2 | Comparative Example 1 |
| copolymer[3] at | | | |
| 2 days | 19.79 | 25.76 | 77.23 |
| 2 days (repeat) | 15.82 | 35.23 | 81.80 |

[1]Glycolic acid
[2]Determined by hot stage microscopy
[3]Determined by measuring weight loss of copolymer after the indicated number of days The data from Table 1 shows a significant increase in the rate of hydrolysis for the copolymers of this invention compared to prior art copolymers of ε-caprolactone and glycolide. The rate of hydrolysis is a measure of the rate of absorption since synthetic copolymers degrade via hydrolysis.

A 10 and 15 percent coating solution of each of the copolymers of Examples 1 and 2, and Comparative Example 1, in toluene is prepared. A size 2/0 (USP standard) Vicryl® poly(lactide-co-glycolide) braided multifilament suture is coated with each coating solution using conventional laboratory coating equipment. The physical properties of the coated sutures are evaluated and the results are reported in Table 2 as Examples 3, 4, and Comparative Example 2, which correspond to Examples 1, 2, and Comparative Example 1, respectively.

TABLE 2

| PHYSICAL PROPERTIES OF SUTURES COATED WITH COPOLYMERS | | | | | | |
|---|---|---|---|---|---|---|
| | Example No. | | | | | |
| | 3 | | 4 | | Comparative Example 2 | |
| | 10% Sol. | 15% Sol. | 10% Sol. | 15% Sol. | 10% Sol. | 15% Sol. |
| | caprolactone/ glycolide/GA[1] Copolymer 90/5/10 by mole IV = 0.19 dl/g | | caprolactone/ glycolide/GA[1] copolymer 90/8/4 by mole IV = 0.31 dl/g | | caprolactone/ glycolide/GA[1] copolymer 90/10/0 by wt. (90/10/0 by mole) IV = 0.28 dl/g | |
| Dia., (mils) | 12.6 | 12.7 | 12.8 | 12.7 | 12.9 | 12.9 |
| Tissue Drag[2], gms | 18.34 | 22.13 | 22.13 | 17.00 | 32.25 | 14.54 |
| Wet Roughness Tiedown[3], gms | 310.32 | 353.98 | 137.89 | 113.41 | 149.66 | 124.40 |
| Percent Elong.[4] | 17.7 | 18 | 16.6 | 17.3 | 17.6 | 17.3 |
| Dry Knot Tensile[4], psi | 73,800 | 72,600 | 73,800 | 69,500 | 71,900 | 68,800 |
| Wet Knot Tensile[4], psi | 75,400 | 71,800 | 73,000 | 71,000 | 71,900 | 70,400 |
| Dry Str. Tensile[4], psi | 124,300 | 121,600 | 116,600 | 119,200 | 112,500 | 113,200 |

[1]Glycolic acid
[2]Tissue Drag is a measure of the relative smoothness of the suture while passing through tissue, and is determined by using an Instron Tensile Tester and a recording device.
[3]Tiedown measured on a Table-Model Instron Tensile Tester as described in U.S. Pat. No. 3,942,532.
[4]Tensile properties and elongation determined generally according to the procedures outlined in U.S. Pat. No. 4,838,267. Wet tensile properties were measured after immersing the coated suture in water at 25° C. for 24 hours.

The data from Table 2 illustrates comparable physical properties achieved for sutures coated with the copolymers of this invention relative to the physical properties of sutures coated with prior art copolymers of ε-caprolactone and glycolide.

Similar outstanding results can be obtained by varying the mole ratio of each of the comonomer components of the copolymer. A coated suture with tailor-made properties can be prepared by selecting an appropriate multifilament suture with the desired coating copolymer.

We claim:

1. A copolymer of a predominant amount of ε-caprolactone and the balance glycolide and glycolic acid, at a concentration of glycolic acid such that the intrinsic viscosity of the copolymer in hexafluoroisopropyl alcohol is between about 0.15 to about 0.60 dl/g.

2. The copolymer of claim 1 wherein the amount of ε-caprolactone is between about 80 to about 95 mole percent.

3. The copolymer of claim 2 wherein the amount of ε-caprolactone is between about 90 to about 95 mole percent.

4. The copolymer of claim 3 wherein the intrinsic viscosity of the copolymer is between about 0.20 to about 0.50 dl/g.

5. The copolymer of claim 4 wherein the melting temperature of the copolymer is between about 35° to about 50° C.

6. The copolymer of claim 5 wherein the amount of glycolic acid is between about 1 to about 15 mole percent.

7. The copolymer of claim 6 wherein the amount of glycolide is between about 2 to about 10 mole percent.

8. A coating for a surgical suture comprising a solution of the copolymer of claim 1 or 7 in an organic solvent.

9. The coating of claim 8 wherein the amount of copolymer in solution is between about 1 to about 20 weight percent.

10. The coating of claim 9 wherein the suture is an absorbable monofilament or multifilament suture with or without an attached needle.

11. The coating of claim 10 wherein the suture is an absorbable multifilament suture.

12. The coating of claim 11 wherein the absorbable multifilament suture is in the form of a braid.

13. The coating of claim 12 wherein the suture is prepared from a polymer of a lactone or one or more lactones.

14. The coating of claim 13 wherein the multifilament suture is a poly(lactide-co-glycolide) braided multifilament suture.

15. An absorbable multifilament suture coated with the copolymer of claim 1.

16. An absorbable multifilament suture coated with the copolymer of claim 7.

* * * * *